(12) United States Patent
Kobayashi et al.

(10) Patent No.: US 10,228,342 B2
(45) Date of Patent: Mar. 12, 2019

(54) SOLID ELECTROLYTE BODY AND GAS SENSOR

(71) Applicant: DENSO CORPORATION, Kariya, Aichi-pref. (JP)

(72) Inventors: Kiyomi Kobayashi, Kariya (JP); Kazuki Yagi, Kariya (JP); Makoto Noguchi, Kariya (JP)

(73) Assignee: DENSO CORPORATION, Kariya (JP)

( * ) Notice: Subject to any disclaimer, the term of this patent is extended or adjusted under 35 U.S.C. 154(b) by 107 days.

(21) Appl. No.: 14/964,632

(22) Filed: Dec. 10, 2015

(65) Prior Publication Data

US 2016/0169830 A1    Jun. 16, 2016

(30) Foreign Application Priority Data

Dec. 10, 2014 (JP) ................................. 2014-249828

(51) Int. Cl.
*G01N 27/407* (2006.01)

(52) U.S. Cl.
CPC ................ *G01N 27/4073* (2013.01)

(58) Field of Classification Search
CPC ............ G01N 27/4073; G01N 27/407; G01N 27/406–27/41; G01N 33/0004–33/0075

(Continued)

(56) References Cited

U.S. PATENT DOCUMENTS

| | | | |
|---|---|---|---|
| 4,328,294 A * | 5/1982 | Tanaka | C04B 35/486 |
| | | | 204/424 |
| 5,122,487 A * | 6/1992 | Hayakawa | C04B 35/486 |
| | | | 423/608 |

(Continued)

FOREIGN PATENT DOCUMENTS

| | | |
|---|---|---|
| JP | 53-139595 | 12/1978 |
| JP | 2003-089576 | 3/2003 |

(Continued)

OTHER PUBLICATIONS

Martin et al. (M.C. Martin, M.L. Mecartney, Grain boundary ionic conductivity of yttrium stabilized zirconia as a function of silica content and grain size, Solid State Ionics, 161 (2003) 67-79).*

(Continued)

*Primary Examiner* — Maris R Kessel
*Assistant Examiner* — Joshua L Allen
(74) *Attorney, Agent, or Firm* — Nixon & Vanderhye P.C.

(57) ABSTRACT

A gas sensor has a gas sensor element which has a solid electrolyte body, a reference electrode and a measuring electrode. The solid electrolyte body contains partially stabilized zirconia as a main component in which zirconia is stabilized by stabilizer agent. Particle boundary parts are formed between crystal particles made of the partially stabilized zirconia. The particle boundary parts are made of a metal element such as yttria derived from the stabilizer agent, an alumina component and a silica component. A total content of the alumina component and the silica component in the particle boundary parts in the solid electrolyte body is within a range of 0.01 mass % to 1 mass % in terms of oxide in the solid electrolyte body. A ratio of the alumina component to the silica component in the particle boundary parts 12 is within a range of 0.2 to 2.0 in terms of oxide.

8 Claims, 4 Drawing Sheets

(58) Field of Classification Search
USPC .................................................. 204/421, 424
See application file for complete search history.

(56) References Cited

U.S. PATENT DOCUMENTS

| | | | | |
|---|---|---|---|---|
| 5,419,827 | A * | 5/1995 | Nanataki | C04B 35/486 204/421 |
| 6,174,489 | B1 * | 1/2001 | Kobayashi | G01N 27/4073 264/618 |
| 2002/0008024 | A1 * | 1/2002 | Sugiyama | C04B 35/117 204/426 |
| 2002/0139670 | A1 * | 10/2002 | Beckmeyer | G01N 27/4071 204/429 |

FOREIGN PATENT DOCUMENTS

| | | |
|---|---|---|
| JP | 2004-003998 | 1/2004 |
| JP | 2004003998 A * | 1/2004 |
| JP | 2004-143031 | 5/2004 |

OTHER PUBLICATIONS

Tsuzuki et al. (JP 2004003998 A, machine translation).*
Badwal et al. (S.P.S. Badwal, Effect of dopant concentration on the grain boundary and volume resistivity of yttria-zirconia, J. Mater. Sci. Lett. 6 (1987) 1419-1421. (Year: 1987).*
Evans et al. (N. D. Evans, P.H. Imamura, J. Bentley, M.L. Mecartney, Characterization of intergranular phases in doped zirconia polycrystals, Mat. Res. Soc. Symp. Proc. 589 (2001) 383-388) (Year: 2001).*
Matsui, "Sintering mechanism in yttria-stabilized zirconia: grain-boundary-segregation effect of yttrium (III) ions" *TOSOH Research & Technology Review*, vol. 55: 7-18 (2011) http://www.tosoh.co.jp/technology/assets/2011_02_02.pdf.

* cited by examiner

SOLID ELECTROLYTE BODY AND GAS SENSOR

CROSS-REFERENCE TO RELATED APPLICATION

This application is related to and claims priority from Japanese Patent Application No. 2014-249828 filed on Dec. 10, 2014, the contents of which are hereby incorporated by reference.

BACKGROUND OF THE INVENTION

1. Field of the Invention

The present invention relates to solid electrolyte bodies having oxygen ion conductivity and gas sensors having a gas sensor element equipped with the solid electrolyte body.

2. Description of the Related Art

A gas sensor detects a concentration of a specific gas such as oxygen gas contained in a mixture gas such as exhaust gas emitted from internal combustion engines. Such a gas sensor uses a solid electrolyte body having oxygen ion conductivity. In more detail, a gas sensor is equipped with a gas sensor element, a heater section, etc. The gas sensor element has a solid electrolyte body and a pair of electrodes. For example, the electrodes are formed on both surfaces of the solid electrolyte body, respectively. When receiving electric power, the heater section generates heat energy. The generated heat energy heats the gas sensor element, and a temperature of the gas sensor element rises. A patent document, Japanese patent laid open publication No. S53-139595 has disclosed such a gas sensor having such a conventional structure. In particular, it is requested for the solid electrolyte body in the gas sensor element to have and maintain specific functions, such as a highly operational reliability and a quick responsiveness to a change of a concentration of a target gas to be detected, without causing cracks under harsh environment.

Also, a zirconia sintered body has been developed as a solid electrolyte body to be used in gas sensor element. The zirconia sintered body contains oxygen ion conductive material and a zirconia sintered body. In the solid electrolyte body, the oxygen ion conductive material and zirconia sintered body are mixed under a predetermined compound ratio. The oxygen ion conductive material is made of zirconium oxide and yttrium oxide which have been mixed in a predetermined compound ratio. The zirconia sintered body is made of aluminum oxide and silicon oxide which have been mixed in a predetermined compound ratio.

Recently, there is a strong demand to save a fuel consumption of internal combustion engines mounted on vehicles, etc. and an increasing requirement to provide a gas sensor with highly quick responsiveness under low temperature environment. However, there is a possible problem of causing cracks in a gas sensor equipped with the conventional solid electrolyte body, and having a low responsiveness when the gas sensor is used at a low temperature of approximately not more than 350° C. That is, low temperature deterioration occurs in the conventional solid electrolyte body.

SUMMARY

It is therefore desired to provide a solid electrolyte body, a gas sensor element using the solid electrolyte body and a gas sensor equipped with the gas sensor element having a quick responsiveness at a low temperature and preventing low temperature deterioration.

An exemplary embodiment provides a solid electrolyte body having partially stabilized zirconia as a main component of the solid electrolyte body. The partially stabilized zirconia is stabilized by stabilizer agent. In the solid electrolyte body, particle boundary parts are formed between crystal particles made of the partially stabilized zirconia. The particle boundary parts are made of a metal element derived from the stabilizer agent, an alumina component and a silica component. In particular, a total content of the alumina component and the silica component in the particle boundary parts in the solid electrolyte body is within a range of 0.01 mass % to 1 mass % in terms of oxide in a total content of the solid electrolyte body. Further, a ratio of the alumina component to the silica component in the particle boundary parts 12 is within a range of 0.2 to 2.0 in terms of oxide.

Another exemplary embodiment provides a gas sensor element having a reference electrode, a measuring electrode, and the solid electrolyte body. Further, another exemplary embodiment provides a gas sensor equipped with the gas sensor element having the reference electrode, the measuring electrode, and the solid electrolyte body In the solid electrolyte body according to the exemplary embodiment of the present invention, a composition of the alumina component (Al) and the silica (Si) component in the particle boundary parts is adjusted within the specific range previously described, where the particle boundary parts are formed between particles made of partially stabilized zirconia. The total content of the alumina component (Al) and the silica (Si) component, in terms of oxide, in the particle boundary parts in the solid electrolyte body is adjusted to be within the predetermined specific low range, i.e. within a range of 0.01 mass % to 1 mass % in terms of oxide in the solid electrolyte body. In addition to this feature, the ratio of the alumina component (Al) to the silica (Si) component, in terms of oxide, in the particle boundary parts is also adjusted within the predetermined specific range, i.e. within a range of 0.2 to 2.0 in terms of oxide, as previously described. The solid electrolyte body according to the exemplary embodiment of the present invention having this structure has excellent features capable of preventing the solid electrolyte body from breaking and generating cracks at a low temperature. In addition to the features, the solid electrolyte body is capable of suppressing the electrical resistance of the solid electrolyte body from increasing under a low temperature condition. It is possible for the present invention to provide the gas sensor having a highly sensor responsiveness and capable of preventing deterioration at a low temperature when the gas sensor is equipped with the gas sensor element having the solid electrolyte body having the improved structure previously described.

That is, it can be considered that electrical resistance of the solid electrolyte body is determined based mainly on a particle boundary resistance between the crystal particles made of partially stabilized zirconia. Accordingly, it is effective to improve the sensor responsiveness at a low temperature by reducing a total content of alumina component (Al) and the silica (Si) component which form the particle boundary parts. On the other hand, from the viewpoint of preventing breaking of the solid electrolyte body and deterioration of the solid electrolyte body under the low temperature condition, it is particularly necessary for the solid electrolyte body to contain silica having a specific content. Therefore, as previously described, when the solid electrolyte body has the specific structure which has the specific range of the total content of the alumina component (Al) and the silica (Si) component, and the specific range of the ratio of the alumina component (Al) to the silica (Si) component in the particle boundary parts, it is possible to provide the solid electrolyte body capable of preventing the low temperature deterioration of the solid electrolyte body, improving a durability of the solid electrolyte body and having a superior sensor responsiveness at a low temperature.

As previously described and will be explained in the following exemplary embodiments, the present invention provides the solid electrolyte body, the gas sensor element and the gas sensor capable of preventing the low temperature deterioration and the superior sensor responsiveness at a low temperature.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Figure 1:
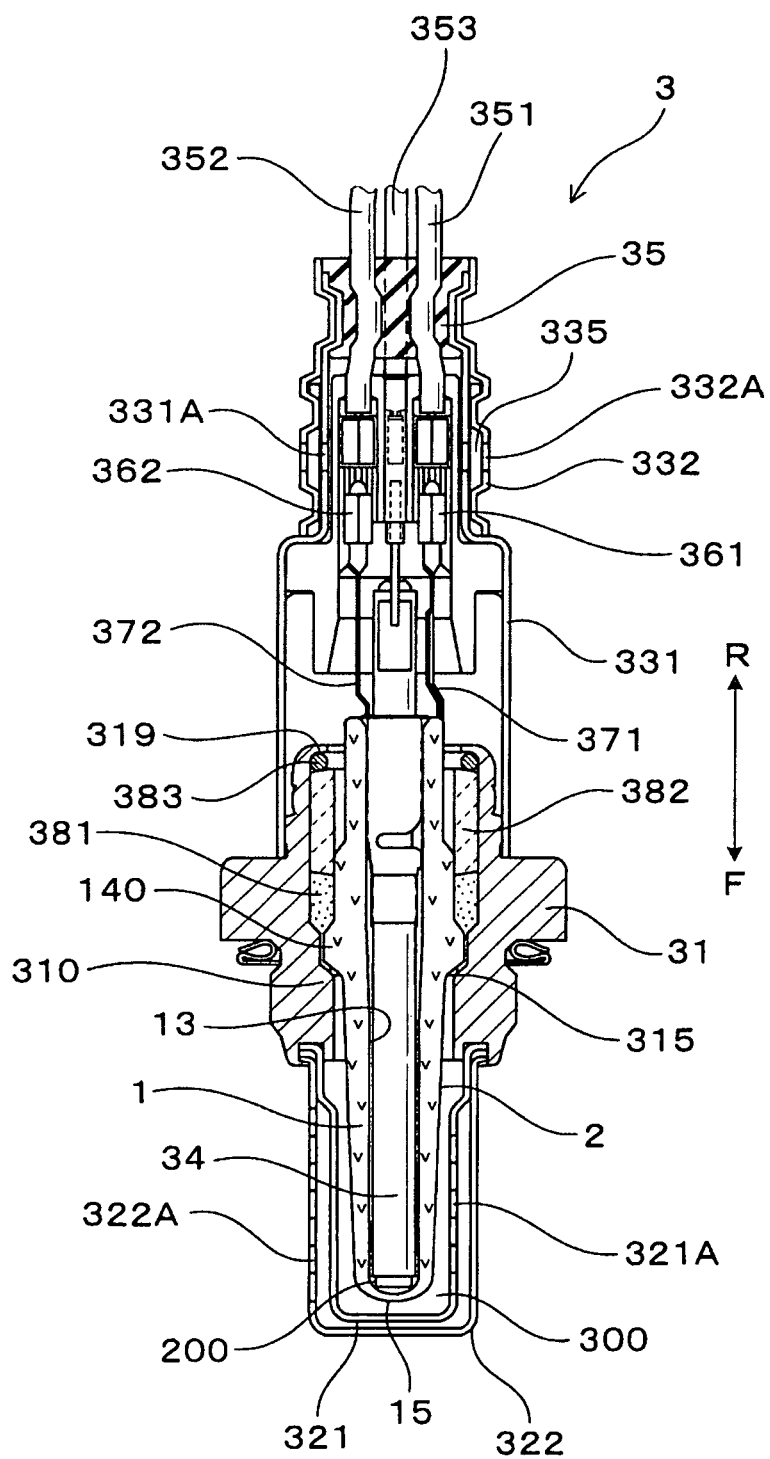
FIG. 1 is a view showing a cross section of a gas sensor equipped with a gas sensor element having a solid electrolyte body according to a first exemplary embodiment of the present invention.

Hereinafter, various embodiments of the present invention will be described with reference to the accompanying drawings. In the following description of the various embodiments, like reference characters or numerals designate like or equivalent component parts throughout the several diagrams.

First Exemplary Embodiment

A description will now be given of a solid electrolyte body 1 and a gas sensor 3 according to a first exemplary embodiment with reference to FIG. 1 to FIG. 4.

FIG. 1 is a view showing a cross section of the gas sensor 3 equipped with the gas sensor element 2 having the solid electrolyte body 1 according to a first exemplary embodiment. As shown in FIG. 1, the gas sensor 3 is equipped with the gas sensor element 2. The gas sensor element 2 is equipped with the solid electrolyte body 1.

As shown in FIG. 1, the gas sensor 3 according to the first exemplary embodiment is mounted to an exhaust gas passage system of a vehicle, for example. The gas sensor 3 is arranged on an exhaust gas passage through which exhaust gas emitted from an internal combustion engine of the vehicle is exhausted outside. The gas sensor 3 is an air fuel ratio sensor. The gas sensor 3 is equipped with the gas sensor element 2 having the solid electrolyte body 1 according to the first exemplary embodiment.

Figure 2:
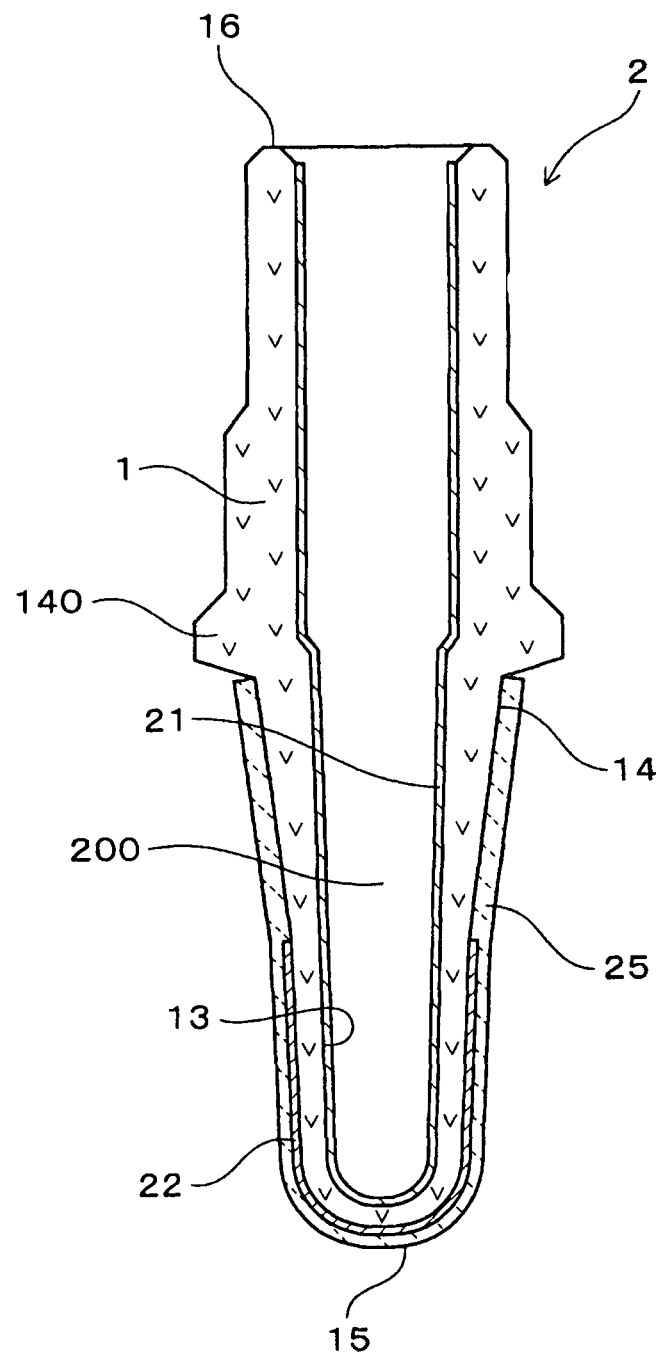
FIG. 2 is a view showing a cross section of the solid electrolyte body in the gas sensor element in the gas sensor according to the first exemplary embodiment shown in FIG. 1.

FIG. 2 is a view showing a cross section of the solid electrolyte body 1 in the gas sensor element 2 in the gas sensor 3 according to the first exemplary embodiment shown in FIG. 1.

As shown in FIG. 2, the gas sensor element 2 has the solid electrolyte body 1, a reference gas side electrode (reference electrode) 21 and a measurement gas side electrode (measuring electrode) 22.

The solid electrolyte body 1 is made of partially stabilized zirconia (PSZ) such as yttria-stabilized zirconia (YSZ), etc. The reference electrode 21 and the measuring electrode 22 are made of metal. The measurement gas is a gas to be measured by the gas sensor 3. A description will now be given of the reference electrode 21 and the measuring electrode 22 in the gas sensor element 2 in detail.

As shown in FIG. 2, the solid electrolyte body 1 in the gas sensor element 2 has a bottomed cylindrical shape (or a cup shape). A reference gas chamber 200 is formed in the solid electrolyte body 1. The solid electrolyte body 1 is made of partially stabilized zirconia (PSZ) such as yttria-stabilized zirconia (YSZ), etc. It is possible for the solid electrolyte body 1 to have a thickness within a range of 0.1 mm to 3 mm.

The reference electrode 21 is made of platinum (Pt) and formed on the inside surface 13 of the solid electrolyte body 1 having a cup shape. The reference electrode 21 is exposed directly to atmosphere as the reference gas. For example, the reference electrode 21 is formed on the overall inside surface 13 of the solid electrolyte body 1.

The measuring electrode 22 is made of platinum (Pt) and formed on the outside surface of the solid electrolyte body 1. The measuring electrode 22 is exposed directly to exhaust gas as the measurement gas. In more detail, the measuring electrode 22 is formed on an area of the outer surface area of the solid electrolyte body 1 measured from the front end part 15 by a predetermined length. The reference electrode 21 and the measuring electrode 22 are arranged opposite to each other on the solid electrolyte body 1. A lead electrode is formed in the measuring electrode 22 toward a rear end side 16 of the solid electrolyte body 1. The rear end side of the lead electrode is electrically connected to a terminal electrode. The lead electrode and the terminal electrode are not shown in FIG. 2. The measuring electrode 22 is covered with a porous protection layer 25. The porous protection layer 25 is made of spinel type oxide such as $MgAl_2O_4$ as a main component of the porous protection layer 25. The porous protection layer 25 is capable of trapping harmful components contained in measurement gas such as exhaust gas emitted from an internal combustion engine mounted on a vehicle.

As shown in FIG. 1, the gas sensor 3 is composed of a cylindrical housing 31 and the gas sensor element 2. The cylindrical housing 31 is made of metal. The gas sensor element 2 is inserted and fixed to the inside of the cylindrical housing 31. In the following explanation, the front side of the gas sensor 3 is inserted to the exhaust gas pipe of the internal combustion engine. The front side of the gas sensor is represented by reference character F shown in FIG. 1. The distal end side of the gas sensor 3 is designated by reference character R shown in FIG. 1. A measurement gas side covers 321 and 322 are arranged at the front end side of the cylindrical housing 31 in order to protect the front side 15 of the gas sensor element 2. That is, the measurement gas side covers 321 and 322 form a dual structure. A measurement gas chamber 300 is formed in the inside of the measurement gas side covers 321 and 322. Further, introduction holes 321A and 322A are formed in the measurement gas side covers 321 and 322. The measurement gas such as exhaust gas is introduced into the inside of the measurement gas chamber 300 through the introduction holes 321A and 322A. The measurement gas atmosphere is formed in the measurement gas chamber 300.

On the other hand, atmosphere side covers 331 and 332 are formed at the distal end side of the cylindrical housing 31. The atmosphere side covers 331 and 332 have a dual structure. The inside of the atmosphere side covers 331 and 332 is interconnected to the reference chamber 200 formed in the solid electrolyte body 1. Introduction holes 331A and 332A are formed in the atmosphere side covers 331 and 332, respectively, so that the introduction holes 331A and 332A face to each other. Through the introduction holes 331A and 332A, the reference gas (atmosphere such as air) is introduced into the reference chamber 200.

A water repellent filter 335 is arranged between the introduction hole 332A and the introduction hole 331A. The atmosphere such as air passes through the water repellent filter 335 and the introduction hole 331A, and introduced into the inside of the reference chamber 200. The air atmosphere is generated in the inside of the reference chamber 200.

As shown in FIG. 1, a bar-shaped heater 34 (hereinafter, the heater 34) is inserted and arranged to the inside of the reference chamber 200 of the gas sensor element 2. A gap having a predetermined length is formed between a side surface of the heater 34 and the inner surface 13 of the solid electrolyte body 1. A front end of the heater 34 is in contact with the inner surface 13 of the solid electrolyte body 1.

An elastic insulation member 35 is formed at the distal end side of the atmosphere side covers 331 and 332. Lead wires 351, 352 and 353 are inserted into the gas sensor 3 through the elastic insulation member 35. Electric signal of the gas sensor element 2 is generated on is the basis of a difference in oxygen concentration between the reference chamber 200 and the measurement gas chamber 300. The electric signal generated in the gas sensor element 2 is transmitted to an outside device (not shown) through the lead wires 351 and 352. When receiving electric power from electric power source (not shown) through the lead wire 353, the heater 34 generates heat energy, and the generated heat energy increases a temperature of the solid electrolyte body 1.

Connection terminals 361 and 362 are arranged at the front end side of the lead wires 351 and 352. The lead wires 351 and 352 are electrically connected to terminals 371 and 372 fixed to the gas sensor element 2 by the Connection terminals 361 and 362.

As shown in FIG. 1 and FIG. 2, the terminal 371 is electrically connected and fixed to a terminal electrode which is connected to the measuring electrode 22 in the gas sensor element 2. The terminal 372 is in contact with and fixed to the reference electrode 21 of the gas sensor element 2. The reference electrode 21, the measuring electrode 22 and the protection layer 25, etc. are omitted from FIG. 2 for brevity.

As shown in FIG. 1 and FIG. 2, a protruding part 140 is formed on the outer surface 14 of the solid electrolyte body 1 in the gas sensor element 2. The protruding part 140 protrudes toward a radially outer direction of the gas sensor element 2. A supporting section 310 is formed in the housing 31. The supporting section 310 protrudes from the inner surface of the housing 31 toward a radially inside direction. The supporting section 310 supports the protruding part 140.

A metal packing 315 is arranged between the front end side of the protruding part 140 and the supporting section 310. A filler section 381 and an insulating glass 382 are arranged between the gas sensor element 2 and the housing 31. The filler section 381 is made of powder filling member such as talc. When the end section 319 at the distal end side of the housing 31 is caulked, the side surface at the distal end side of the insulation glass 382 is fixed by the metal ring 383.

A description will now be given of a structure of the solid electrolyte body 1 used in the gas sensor element 2 according to the first exemplary embodiment in detail with reference to FIG. 3 and FIG. 4.

Figure 3:
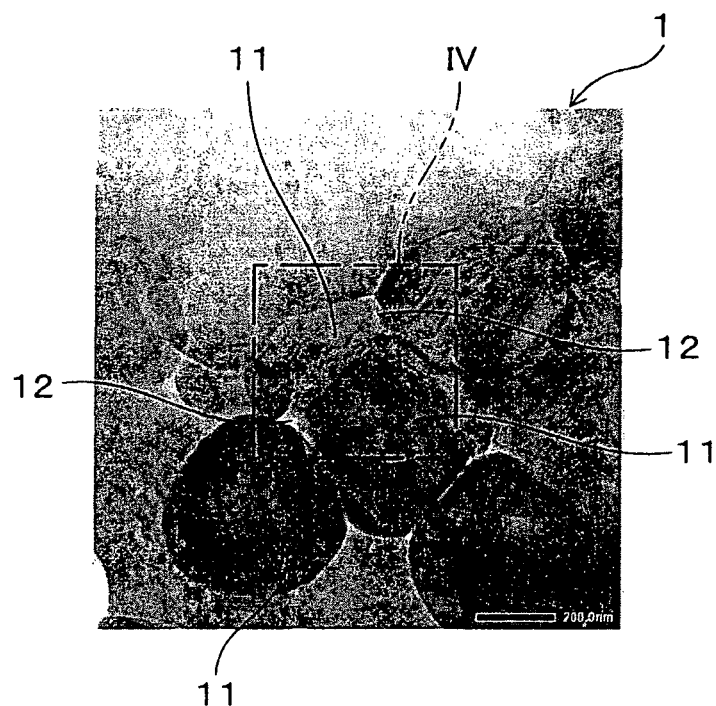
FIG. 3 is a view showing a photograph of the solid electrolyte body, obtained by a scanning electron microscope (SEM), used in the gas sensor according to the first exemplary embodiment shown in FIG. 1.

FIG. 3 is a view showing a photograph of the solid electrolyte body, obtained by a scanning electron microscope (SEM), used in the gas sensor according to the first exemplary embodiment shown in FIG. 1. FIG. 4 is an enlarged view showing an area IV in the photograph of the solid electrolyte body shown in FIG. 3.

The solid electrolyte body 1 according to the first exemplary embodiment is made of partially stabilized zirconia (PSZ) as a main component. The partially stabilized zirconia (PSZ) is obtained by stabilizing zirconia with yttria. As shown in FIG. 3 and FIG. 4, grain boundary parts 12 are formed between crystal particles 11 made of partially stabilized zirconia (PSZ). The grain boundary parts 12 are made of oxide which contains yttria (Y) derived from the stabilized zirconia, alumina (Al) and silica (Si). In general, yttria is used as a stabilizer agent. It is considered that the grain boundary parts 12 are formed by a composite oxide of metal elements yttria (Y), alumina (Al) and silica (Si).

The first exemplary embodiment prepared test samples 1 to 20 and comparative samples 1 to 5. These test samples 1 to 20 and the comparative samples 1 to 5 have a different grain composition by changing a combination of raw materials and an average particle size of the raw materials during the manufacturing process of producing these test samples 1 to 20 and the comparative samples 1 to 5. In Table 1, the test samples 1 to 20 are designated by reference characters TS 1 to TS 20, respectively, and the comparative samples 1 to 5 are designated by reference characters CS 1 to CS 5, respectively.

A description will now be given of the manufacturing method of producing the solid electrolyte body according to the first exemplary embodiment. The test samples 1 to 20 and the comparative samples 1 to 5 were produced by the following manufacturing method.

First, yttria powder was added into zirconia powder as main raw material to prepare a first mixture so that the yttria powder in the first mixture had a content of 8 mass %. Further, alumina powder and silica powder were added into the first mixture to prepare a second mixture by a dry mixing. The second mixture was pulverized to produce a raw powder mixture of a solid electrolyte body. The alumina powder was fine particle $\alpha$-$Al_2O_3$ powder having an average particle size of 0.1 μm. The silica powder was amorphous silica powder having a specific surface area of 50 $m^2$/g. Alumina powder and silica powder were mixed to produce a mixture powder having a uniform powder by using air mixer. In general, it is possible to easily produce a particle boundary phase having a specific composition which will be explained later when alumina powder, and silica powder having a small average particle size are used.

It is possible to form, the grain boundary having a uniform thickness and composition by the following processes.

Alumina powder and silica powder are mixed together, and fired at a temperature of 1200° C. After the mixing and firing process, the mixture is pulverized to produce a mixture powder having a uniform mixture state and particle size. The produced mixture powder is added to zirconia powder and yttria powder to produce a uniform thickness and composition. Further, because alumina powder and silica powder are mixed and fired before added to zirconia powder and yttria powder, it is possible for these processes to reduce a melting point of the mixture powder. As a result, when the raw powder mixture of zirconia powder and yttria powder is fired, it is possible for these alumina particles and silica particles to easily move at a relatively low temperature. As a result, this makes it possible to promote chemical reaction between yttria, alumina and silica, reduce the grain boundary layer, and have uniform composition of the grain boundary layer. Still further, this makes it possible to prepare and use alumina powder and silica powder having relatively large particle size. This reduces a material cost and a production cost.

It is also possible for the raw material to contain α-$Al_2O_3$ powder of not more than 2 mass % and having an average particle size within a range of 0.5 μm to 1.0 μm. Because this case prevents zirconia particles from moving during the firing process, and prevents sintering and crystal growth, it is possible to rise the sintering temperature. As a result, this makes it possible to generate partially stabilized zirconia (PSZ) in which yttria is adequately melted and dispersed.

By the way, α-$Al_2O_3$ powder having a relatively large average particle size is remained as free alumina crystal particles in the grain boundary without reaction with alumina grains, silica grains, and yttria grains. Because being not gathered in the grain boundary, the free alumina crystal particles do not block ion conductivity of the solid electrolyte body, and not increase an internal resistance of the solid electrolyte body. The present invention does not contain free alumina particles as a component to form the particle boundary parts 12.

Next, water was added to the raw powder mixture to produce a slurry of the raw powder mixture. The obtained slurry was pulverized and loosened by using a wet-type vibration mill. Next, the pulverized raw powder mixture was dried by using a rubber press molding to produce granular powder having a cup shape. The molded body having a cup shape was grinded to have a shape of the solid electrolyte body 1 shown in FIG. 2.

Next, the molded body was fired at a temperature of 1400° C. to produce the solid electrolyte body 1 made of partially stabilized zirconia (PSZ) as a main component.

The first exemplary embodiment produced the solid electrolyte body 1 by changing the conditions, i.e. prepared 25 samples such as the test samples 1 to 20 and the comparative samples 1 to 5. These samples were produced by changing the combination of the raw material and average particle size, etc.

The first exemplary embodiment and the second exemplary embodiment used the average particle size indicating a particle size (particle diameter) at a volume integrated value of 50% obtained by laser diffraction scattering method. The second exemplary embodiment will be explained later.

The first exemplary embodiment detects a composition of the grain boundary parts 12 in the solid electrolyte body 1 (each of test samples 1 to 20 and the comparative sample 1 to 5) by using an energy diffraction type X-ray analyzer using a scanning transmission electron microscope (STEM). STEM is a type of transmission electron microscope (TEM). STEM focuses an electron beam into a narrow spot which is scanned over a sample in a raster.

Specifically, a specimen was cut from the solid electrolyte body 1. The specimen is a front end part of the solid electrolyte body 1. The specimen, i.e. the front end part of the solid electrolyte body 1 is exposed to and in contact with the measurement gas such as exhaust gas. A thin film part having a thickness of 0.1 μm was separated from the specimen by using a VION focused ion beam device (manufactured by Japan FEI Corp.) The obtained thin film part was observed by a scanning transmission electron microscope (STEM, JEM-2800 manufactured by JEOL Ltd.). FIG. 3 shows the obtained STEM photograph having 200,000 times in magnification.

Next, five areas IV were optionally selected in the thin film part. Each of the selected areas IV has a 500 nm square. FIG. 4 shows a STEM photograph of the selected area IV (500,000 times in magnification). As shown in FIG. 4, arbitrary ten points were selected in the grain boundary parts 12 in the selected areas IV has a 500 nm square.

Further, five points were selected from two particle boundaries designated by white circles, and five points were selected from three particle boundaries. Because no free alumina crystal particles present in these boundaries, no measurement point was selected from the alumina crystal particles. That is, in FIG. 4, arbitrary points on the two particle boundaries are designated by white circle, and arbitrary points on the three particle boundaries are designated by halftone circles or gray circles. In order to clearly show these three particle boundaries in FIG. 4, a part of the particle boundary part 12 is designated by dotted lines.

Next, qualitative analysis and quantitative analysis of the selected ten points were performed by using EDS analyzer in order to detect a composition of alumina (Al) component, silica (Si) component and yttria (Y) component in terms of oxide. That is, a quantity of each of alumina, silica and yttria in these selected ten points was detected, and an average value of each of the components was calculated.

That is, an average value of the detected values obtained at the arbitrary ten points in each of the five areas IV having a 500 nm square was calculated, and an average value of the five areas IV was calculated. The calculated average value of the five areas IV indicates a content of each component in the particle boundary parts 12. Table 1 shows the calculation results of these components (mass %) in the particle boundary parts 12 in the test samples 1 to 20 (TS1 to TS20) and the comparative samples 1 to 5 (CS1 to CS5).

Next, as shown in FIG. 2, the reference electrode 21 was formed in the solid electrolyte body 1 in each of the test samples 1 to 20 and the comparative samples 1 to 5. The reference electrode 21 was made of platinum (Pt). Further, the measuring electrode 22, the lead wires, and the terminal electrodes were formed on the outer surface of the solid electrolyte body 1 in each of the test samples 1 to 20 and the comparative samples 1 to 5. Further, the protection layer 25 was formed on the solid electrolyte body 1 in each of the test samples 1 to 20 and the comparative samples 1 to 5. These electrodes, the lead wires and the protection layer can be formed by the known method. The gas sensor element 2 was produced by the above method, and the gas sensor 3 equipped with the gas sensor element 2 (which correspond to each of the test samples 1 to 20 and the comparative samples 1 to 5) was produced.

Next, the first exemplary embodiment evaluated a sensor responsiveness of the gas sensor 3 as each of the test samples 1 to 20 and the comparative samples 1 to 5. Further, the first exemplary embodiment evaluated a low temperature deterioration of each of the test samples 1 to 20 and the comparative samples 1 to 5, as follows.

[Sensor Responsiveness]

A temperature of the front side of the gas sensor element 1 was kept at a temperature of 350° C. by using the heater 34 in the gas sensor 3 as each of the test samples 1 to 20 and the comparative samples 1 to 5.

After the temperature at the front side of the gas sensor element 2 became stable, a rich gas was supplied to the gas sensor 3. In this case, the rich gas contained carbon monoxide (CO), methane ($CH_4$), propane ($C_3H_8$) and nitrogen ($N_2$) so that an air fuel (A/F) ratio became 0.97.

Next, a lean gas was supplied to the gas sensor 3 so that the A/F ratio became 1.03. The lean gas contained oxygen ($O_2$), nitrogen oxide (NO), and nitrogen ($N_2$). Nitrogen was a balance gas in the rich gas and the lean gas. Further, the supply of the rich gas and the lean gas was alternately switched at a predetermined time period. The first exemplary embodiment detected a time length counted from a timing when the supply of the rich gas is switched to the supply of the lean gas to a timing when the sensor output was changed by 63%. This detected time length becomes the sensor responsiveness of the gas sensor 3 as each of the test samples 1 to 20 and the comparative samples 1 to 5. Table 1 shows the results of the time length as the sensor responsiveness of the gas sensor 3 as each of the test samples 1 to 20 and the comparative samples 1 to 5.

In table 1, reference character (Excellent) indicates the sensor responsiveness of not more than 300 seconds, reference character (Good) indicates the sensor responsiveness within a range of more than 300 seconds and not more than 400 seconds, and reference character (X) indicates the sensor responsiveness of more than 400 seconds.

[Low Temperature Deterioration]

The first exemplary embodiment used an autoclave tester capable of supplying a high pressure steam to the solid electrolyte bod 1 as each of the test samples 1 to 20 and the comparative samples 1 to 5 in order to expose the solid electrolyte bod 1 to high pressure steam atmosphere. In general, an autoclave is a pressure chamber used to sterilize equipment and supplies by subjecting them to high pressure saturated steam. Specifically, the solid electrolyte bod 1 was exposed to high pressure steam atmosphere at a temperature of 200° C., 1.5 MPa over 10 hours in order to perform a hydrothermal treatment of the test samples 1 to 20 and the comparative samples 1 to 5. After the hydrothermal treatment, the solid electrolyte bod 1 was stained in stain solution and then washed. The obtained solid electrolyte bod 1 was observed by visual observation.

When one or more stains were detected, it is judged that the outer surface of the solid electrolyte bod 1 was damaged because cracks were generated or the solid electrolyte body 1 was broken. This case is designated by reference character (X) in Table 1.

On the other hand, when no stain was generated, it is judged that the outer surface of the solid electrolyte bod 1 was not damaged. This case is designated by reference character O in Table 1.

Table 1 shows the results of the low temperature deterioration of the test samples 1 to 20 and the comparative samples 1 to 5.

It can be considered that cracks and breaking occur in the solid electrolyte body 1 when OH groups attack flux components in the particle boundary parts 12 in the solid electrolyte body 1, and this loosens the grain boundary parts 12. In addition, M phase fine particles in zirconia, which had been fixed by flux components, were released and moved to the outer surface of the solid electrolyte body 1. Further, it can be assumed that this reduces a strength of the solid electrolyte body 1, and easily generates cracks or breaking in the solid electrolyte body 1. In the following Table 1, the test samples 1 to 20 are designated by reference characters TS 1 to TS 20, respectively, and the comparative samples 1 to 5 are designated by reference characters CS 1 to CS 5, respectively.

TABLE 1

| Sample No. | Composition (mass %) of particle boundary parts | | | | Composition ratio (mass ratio) | Sensor responsiveness (ms) at low temperature | | Result of evaluation in low temperature deterioration |
|---|---|---|---|---|---|---|---|---|
| | $Al_2O_3$ | $SiO_2$ | $Y_2O_3$ | $Al_2O_3 + SiO_2$ | $Al_2O_3/SiO_2$ | Response time (ms) | Result of Judgement | |
| TS 1 | 0.035 | 0.16 | 0.04 | 0.195 | 0.219 | 250 | EXCELLENT | GOOD |
| TS 2 | 0.007 | 0.13 | 0.03 | 0.2 | 0.538 | 250 | EXCELLENT | GOOD |
| TS 3 | 0.08 | 0.12 | 0.02 | 0.2 | 0.667 | 260 | EXCELLENT | GOOD |
| TS 4 | 0.095 | 0.105 | 0.04 | 0.2 | 0.9 | 300 | EXCELLENT | GOOD |
| TS 5 | 0.11 | 0.1 | 0.05 | 0.21 | 1.1 | 320 | GOOD | GOOD |
| TS 6 | 0.12 | 0.08 | 0.04 | 0.2 | 1.5 | 350 | GOOD | GOOD |
| TS 7 | 0.13 | 0.07 | 0.04 | 0.2 | 1.857 | 400 | GOOD | GOOD |
| TS 8 | 0.05 | 0.07 | 0.02 | 0.12 | 1.714 | 240 | EXCELLENT | GOOD |
| TS 9 | 0.03 | 0.065 | 0.05 | 0.095 | 0.462 | 240 | EXCELLENT | GOOD |
| TS 10 | 0.02 | 0.035 | 0.03 | 0.055 | 0.571 | 230 | EXCELLENT | GOOD |
| TS 11 | 0.007 | 0.013 | 0.005 | 0.02 | 0.5 | 220 | EXCELLENT | GOOD |
| TS 12 | 0.003 | 0.007 | 0.01 | 0.01 | 0.5 | 220 | EXCELLENT | GOOD |
| TS 13 | 0.1 | 0.2 | 0.04 | 0.3 | 0.5 | 250 | EXCELLENT | GOOD |
| TS 14 | 0.13 | 0.26 | 0.05 | 0.39 | 0.5 | 250 | EXCELLENT | GOOD |
| TS 15 | 0.15 | 0.35 | 0.15 | 0.5 | 0.429 | 270 | EXCELLENT | GOOD |
| TS 16 | 0.23 | 0.45 | 0.2 | 0.68 | 0.511 | 310 | GOOD | GOOD |
| TS 17 | 0.35 | 0.65 | 0.2 | 1 | 0.538 | 400 | GOOD | GOOD |
| TS 18 | 0.065 | 0.13 | 0.1 | 0.195 | 0.5 | 260 | EXCELLENT | GOOD |
| TS 19 | 0.07 | 0.14 | 0.05 | 0.21 | 0.5 | 280 | EXCELLENT | GOOD |
| TS 20 | 0.067 | 0.135 | 0.03 | 0.202 | 0.496 | 300 | EXCELLENT | GOOD |

TABLE 1-continued

| Sample No. | Composition (mass %) of particle boundary parts | | | | Composition ratio (mass ratio) | Sensor responsiveness (ms) at low temperature | | Result of evaluation in low temperature deterioration |
|---|---|---|---|---|---|---|---|---|
| | $Al_2O_3$ | $SiO_2$ | $Y_2O_3$ | $Al_2O_3 + SiO_2$ | $Al_2O_3/SiO_2$ | Response time (ms) | Result of Judgement | |
| CS 1 | 0.002 | 0.003 | 0.005 | 0.005 | 0.5 | 230 | EXCELLENT | X |
| CS 2 | 0 | 0 | 0.2 | 0.000 | — | 220 | EXCELLENT | X |
| CS 3 | 0.8 | 0.4 | 0.2 | 1.200 | 2.000 | 500 | X | GOOD |
| CS 4 | 0.018 | 0.18 | 0.05 | 0.198 | 0.101 | 250 | EXCELLENT | X |
| CS 5 | 0.36 | 0.13 | 0.12 | 0.490 | 2.769 | 450 | X | GOOD |

TS: Test sample and CS: Comparative sample

As shown in Table 1, the test samples 1 to 20 (TS 1 to TS 20) according to the first exemplary embodiment have excellent features capable of preventing deterioration at a low temperature and having a superior sensor responsiveness at a low temperature because a total content of alumina (Al) component and silica (Si) component in the particle boundary parts 12 is within a range of 0.01 mass % to 1 mass %, and a ratio of the alumina (Al) component to the silica (Si) component in the particle boundary parts 12 is within a range of 0.2 to 2.0.

On the other hand, a low temperature deterioration occurred in the solid electrolyte body 1 when a total content of the alumina (Al) component and the silica (Si) component in the particle boundary parts 12 is less than 0.01 mass %, like the comparative samples 1 and 2 (CS 1 and CS 2), and when a ratio of the alumina (Al) component to the silica (Si) component in the particle boundary parts 12 is less than 0.2 mass %, like the comparative sample 4 (CS 4). Further, a long sensor responsiveness at a low temperature occurs when a total content of the alumina (Al) component and the silica (Si) component in the particle boundary parts 12 is more than 1 mass %, like the comparative sample 3 (CS 3), or a ratio of the alumina (Al) component to the silica (Si) component in the particle boundary parts 12 is more than 2.0, like the comparative sample 5 (CS 5).

Accordingly, it can be understood to provide the solid electrolyte body and the gas sensor capable of preventing a low temperature deterioration and having a superior sensor responsiveness at a low temperature when the total content of the alumina (Al) component and the silica (Si) component in the particle boundary parts 12 is within the range of 0.01 mass % to 1.0 mass % in terms of oxide in a total content of the solid electrolyte body, and the ratio of the alumina (Al) component to the silica (Si) component in the particle boundary parts 12 is within a range of 0.2 to 2.0 in terms of oxide.

Further, as can be understood from the results shown in Table 1, it is preferable for the solid electrolyte body to have the ratio of the alumina (Al) component to the silica (Si) component in the particle boundary parts 12 is within a range of 0.2 to 1.0 in terms of oxide. This structure makes it possible to improve and increase the sensor responsiveness of the gas sensor at a low temperature.

Still further, as can be understood from the results shown in Table 1, it is preferable for the solid electrolyte body to have the total content of the alumina (Al) component and the silica (Si) component in the particle boundary parts 12 is within the range of 0.01 mass % to 0.5 mass % in terms of oxide in the total content of the solid electrolyte body. This structure also makes it possible to improve and increase the sensor responsiveness of the gas sensor at a low temperature.

Although yttria (Y) component in terms of stabilizer, alumina (Al) component and silicon (Si) component as metal elements are present in the particle boundary parts 12, it is acceptable for the particle boundary parts 12 to contain other components of a very small quantity other than yttria (Y) component derived from the stabilizer agent, alumina (Al) component and silicon (Si) component.

Figure 4:
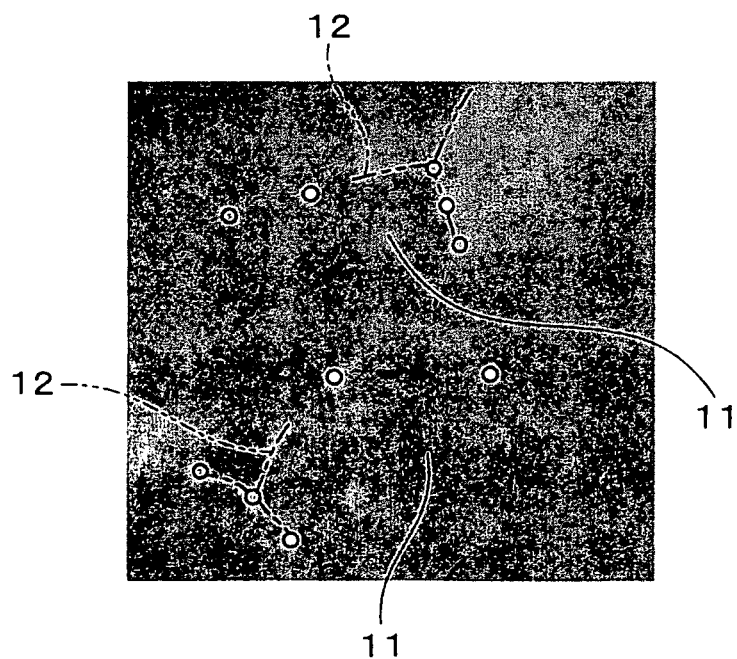
FIG. 4 is an enlarged view showing an area IV in the photograph of the solid electrolyte body shown in FIG. 3.

Still further, as shown in FIG. 3 and FIG. 4, the particle boundary parts are formed between the crystal particles 11 made of partially stabilized zirconia (PSZ). The particle boundary parts are made of oxide which contains the metal element derived from the stabilizer agent, alumina (Al) and silica (Si). It is preferable to use yttria (Y) as the metal element derived from the stabilizer agent. This structure makes it possible to increase ion conductivity of the solid electrolyte body 1, and provide the gas sensor having a strong strength. It is also possible to use, as stabilizer f zirconia, rare earth oxide such as ceria, etc., calcia, magnesia, etc. in addition to yttria. It is also possible to use one or not less than two kinds of the compounds previously described.

Second Exemplary Embodiment

A description will be given of a gas sensor element 2-1 having a stack structure (i.e. a plate type) according to a second exemplary embodiment with reference to FIG. 5.

Figure 5:
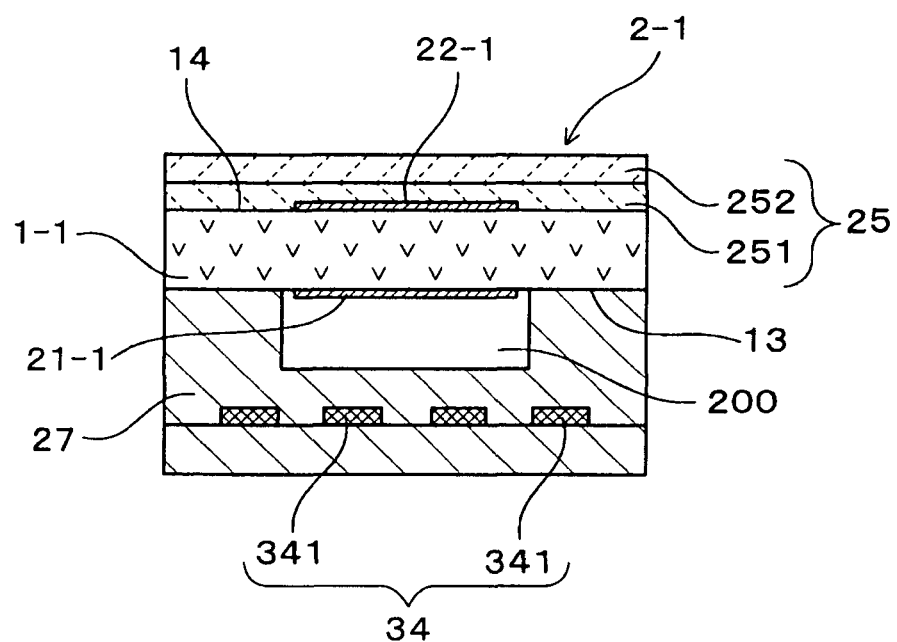
FIG. 5 is a view showing a cross section of a gas sensor element according to a second exemplary embodiment of the present invention.

FIG. 5 is a view showing a cross section of the gas sensor element according to the second exemplary embodiment. The first exemplary embodiment shows the gas sensor element of a cup shape previously described. On the other hand, the gas sensor element 2-1 according to the second exemplary embodiment has a stack structure.

As shown in FIG. 5, the gas sensor element 2-1 according to the second exemplary embodiment has a reference electrode 21-1 and a measuring electrode 22-1. The reference electrode 21-1 is formed on one surface (i.e. a first surface) 13 of the solid electrolyte body 1-1. The measuring electrode 22-1 is formed on the other surface (i.e. a second surface) 14 of the solid electrolyte body 1-1. The reference electrode 21-1 formed on the first surface 13 and the second surface 14 formed on the second surface 14 are faced to each other in a stacked direction. A spacer 27 forms the reference gas chamber 200. Four heating elements 341 are formed and embedded in a back surface of the spacer 27. Four heating elements 341 form the heater section 34. In particular, the measuring electrode 22-1 is covered with a first protection layer 251 and a second protection layer 252. The first protection layer 251 and the second protection layer 252 form a dual protection structure.

It is possible for the solid electrolyte body 1-1 according to the second exemplary embodiment to have the same behavior and effects of the solid electrolyte body 1 according to the first exemplary embodiment when the solid electrolyte body 1-1 has the same composition disclosed by the test samples 1 to 20 previously described.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A solid electrolyte body comprising partially stabilized zirconia as a main component of the solid electrolyte body as a manufactured product in which zirconia is stabilized by stabilizer agent, wherein particle boundary parts are formed between crystal particles made of the partially stabilized zirconia, and the particle boundary parts are made of oxides containing a metal element derived from the stabilizer agent, an alumina component and a silica component, the metal element is yttrium oxide, the alumina component is aluminum oxide, and the silica component is silicon dioxide, the yttrium oxide contained in the particle boundary parts is within a range of 0.005 to 0.2 mass %, and a total content of the aluminum oxide and the silicon dioxide in the oxides contained in the particle boundary parts to a total content of the solid electrolyte body is within a range of 0.01 mass % to 1 mass %, and a ratio of the aluminum oxide to the silicon dioxide in the oxides contained in the particle boundary parts is within a range of 0.2 to 2.0.

2. The solid electrolyte body according to claim 1, wherein the ratio of the aluminum oxide to the silicon dioxide in the oxides contained in the particle boundary parts is within a range of 0.2 to 1.0.

3. The solid electrolyte body according to claim 1, wherein the total content of the aluminum oxide and the silicon dioxide in the oxides contained in the particle boundary parts to the total content of the solid electrolyte body is within a range of 0.01 mass % to 0.5 mass % in terms of oxide in the solid electrolyte body.

4. The solid electrolyte body according to claim 2, wherein the total content of the aluminum oxide and the silicon dioxide in the oxides contained in the particle boundary parts to the total content of the solid electrolyte body is within a range of 0.01 mass % to 0.5 mass % in terms of oxide in the solid electrolyte body.

5. A gas sensor comprising a gas sensor element equipped with the solid electrolyte body according to claim 1.

6. A gas sensor comprising a gas sensor element equipped with the solid electrolyte body according to claim 2.

7. A gas sensor comprising a gas sensor element equipped with the solid electrolyte body according to claim 3.

8. A gas sensor comprising a gas sensor element equipped with the solid electrolyte body according to claim 4.

* * * * *